(12) United States Patent
Pain et al.

(10) Patent No.: US 10,213,227 B2
(45) Date of Patent: Feb. 26, 2019

(54) TRANSCATHETER DEVICE FOR THE ABLATION OF CALCIFIED TISSUE AT THE FLAPS OF AN AORTIC VALVE

(71) Applicants: Centre Hospitalier Universitaire de Saint-Etienne, Saint-Etienne (FR); Aorticlab Sàrl, Savigny (CH)

(72) Inventors: Bernard Pain, Monistrol-sur-Loire (FR); Marco Vola, Saint-Priest-en-Jarez (FR); Enrico Pasquino, Marentino (IT)

(73) Assignee: AorticLab Sàrl, Savigny (CH)

( * ) Notice: Subject to any disclaimer, the term of this patent is extended or adjusted under 35 U.S.C. 154(b) by 263 days.

(21) Appl. No.: 15/315,804

(22) PCT Filed: Jun. 4, 2015

(86) PCT No.: PCT/FR2015/051491
§ 371 (c)(1),
(2) Date: Dec. 2, 2016

(87) PCT Pub. No.: WO2015/185872
PCT Pub. Date: Dec. 10, 2015

(65) Prior Publication Data
US 2017/0100159 A1 Apr. 13, 2017

(30) Foreign Application Priority Data
Jun. 5, 2014 (FR) ..................................... 14 55146

(51) Int. Cl.
*A61B 17/3207* (2006.01)
*A61B 17/22* (2006.01)
(Continued)

(52) U.S. Cl.
CPC .. *A61B 17/320783* (2013.01); *A61B 17/2202* (2013.01); *A61B 17/320758* (2013.01);
(Continued)

(58) Field of Classification Search
CPC ........ A61B 17/320783; A61B 17/2202; A61B 17/320758; A61B 2090/3966;
(Continued)

(56) References Cited

U.S. PATENT DOCUMENTS 5,087,265 A * 2/1992 Summers ....... A61B 17/320758
604/22
5,402,790 A * 4/1995 Jang ........................ A61B 8/12
600/439
(Continued)

FOREIGN PATENT DOCUMENTS

FR 2 882 916 9/2006
WO WO 03/088809 10/2003

OTHER PUBLICATIONS

International Search Report for PCT parent application PCT/FR2015/051491 dated Sep. 1, 2015.
(Continued)

*Primary Examiner* — Julian W Woo
(74) *Attorney, Agent, or Firm* — Andre Roland S.A.; Nikolaus Schibli

(57) ABSTRACT

This transcatheter device for the ablation of calcified tissue at the flaps of an aortic valve, is characterized in that it comprises a flexible body (1) acting as a catheter and having a soft and flexible end piece (2) that engages with a previously inserted wire guide (g) suitable for passing through the flaps of the valve above the part where the calcified tissue needs to be removed, said end piece (2) having at least one cutting system (3) comprising two motorized rotating cutting heads (3a) and (3b) disposed coaxially one above the other, the head (3a) located at the end of the end piece and acting first to remove the calcified tissue, has arrangements suitable for making a rough cut by grinding, while the other head (3b) has arrangements suitable for making a fine cut by grinding, said cutting system
(Continued)

Figure 1:
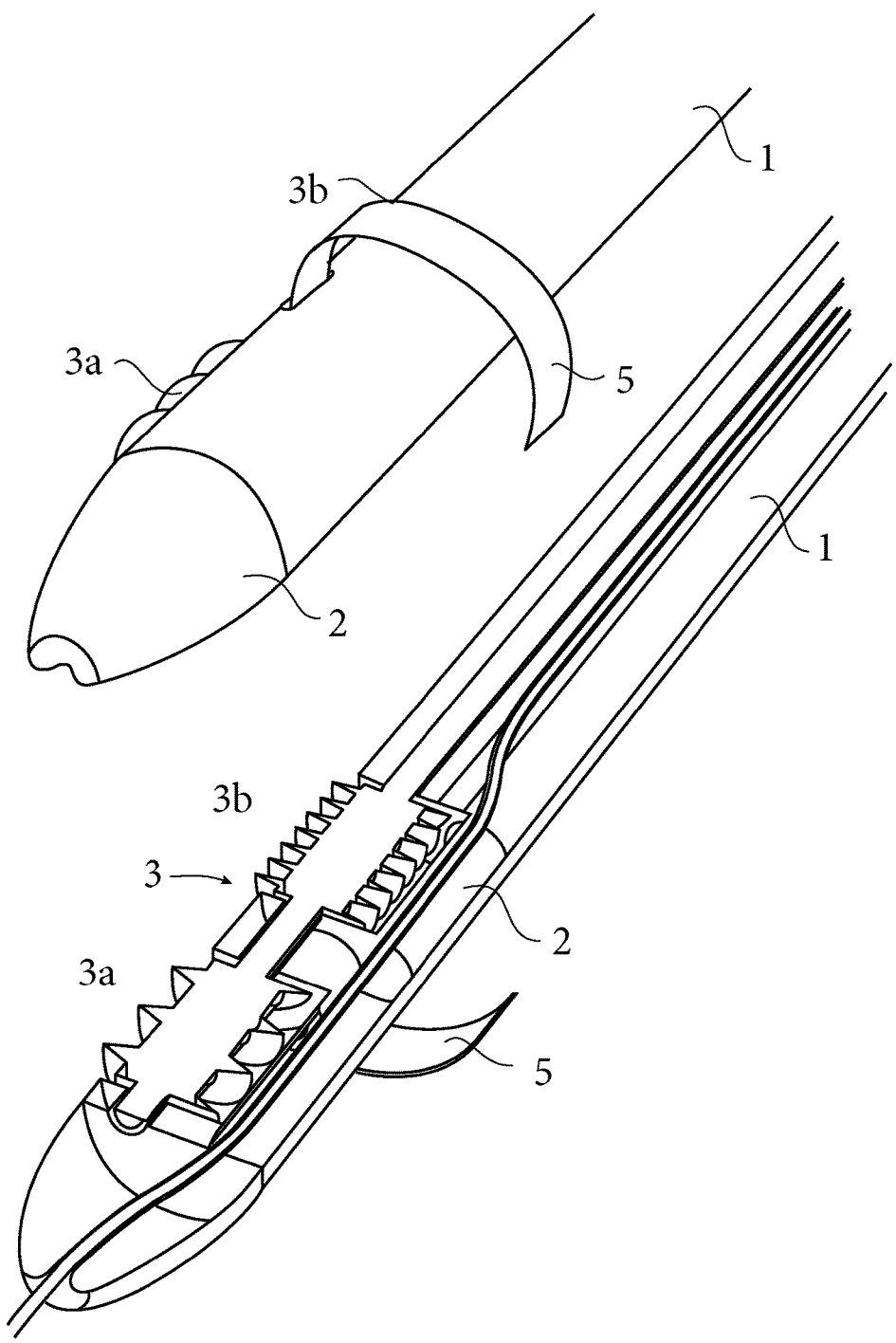

being mounted in combination with a vacuum suction means (4), said end piece (2) being provided with an adjustable guide means (5) suitable for engaging with the calcified tissue over the course of the ablation operation performed by the cutting system (3) in combination with a spiral path effect applied to the end piece.

10 Claims, 16 Drawing Sheets

(51) Int. Cl.
*A61F 2/24* (2006.01)
*A61B 90/00* (2016.01)
(52) U.S. Cl.
CPC .. *A61F 2/2496* (2013.01); *A61B 2017/22038* (2013.01); *A61B 2017/22071* (2013.01); *A61B 2017/22079* (2013.01); *A61B 2017/22098* (2013.01); *A61B 2017/320791* (2013.01); *A61B 2090/3966* (2016.02)

(58) Field of Classification Search
CPC ........... A61B 2017/22079; A61B 2017/22038; A61B 2017/320791; A61B 2017/22098; A61B 2017/22071; A61F 2/2496
USPC .................................................. 606/159, 180
See application file for complete search history.

(56) References Cited

U.S. PATENT DOCUMENTS

| | | | |
|---|---|---|---|
| 6,299,623 B1 * | 10/2001 | Wulfman | A61B 17/320758 606/159 |
| 8,388,635 B2 * | 3/2013 | Kumoyama | A61B 17/320758 606/159 |
| 2004/0049215 A1 | 3/2004 | Snow | |
| 2008/0281232 A1 | 11/2008 | Lansac et al. | |

OTHER PUBLICATIONS

Written Opinion from the International Search Authority for PCT parent application PCT/FR2015/051491 dated Sep. 1, 2015 and English translation.

* cited by examiner

TRANSCATHETER DEVICE FOR THE ABLATION OF CALCIFIED TISSUE AT THE FLAPS OF AN AORTIC VALVE

CROSS REFERENCE TO RELATED APPLICATIONS

The present application is a U.S. national stage application of PCT/FR2015/051491 filed on Jun. 4, 2015 designating the United States, and claims foreign priority to French patent application FR 1455146 filed on Jun. 5, 2014, the contents of both documents being herewith incorporated by reference in their entirety.

The invention relates to surgery and interventional cardiology and more particularly to a transcatheter device for the ablation of calcified tissues, in particular of heart valves.

It is well known that severe disease of the aortic valves is mainly the result of degenerative calcification of the valve, which calcification increases with age. Therefore, when the valves become severely stenotic and clinically symptomatic, it is necessary to intervene surgically in order to replace the valve or to implant a valve by a transcatheter route, known by the acronym TAVI.

It has been found that the implantation of an aortic valve by TAVI through a calcified aortic valve very often causes paravalvular leaks in cases where there is an excessive and poorly balanced concentration of calcium cores. These leaks can have an impact on the life expectancy of the patient. Another complication resulting from the presence of calcium during TAVI is that of embolization, which can cause a coronary embolism, generating an infarction during the procedure, or a cerebral embolism, which leads to iatrogenic strokes, which are caused by the TAVI and which are one of the limits of this technique.

Clinical trials have also shown that at least 10% of patients have a bicuspid aortic valve condition during an electrocardiogram. The morphology of a bicuspid valve is a condition limiting the success of TAVI. The reason for this is that, in the case of a bicuspid aortic valve, the mineralization of the tissues is asymmetric, with a very high and oddly distributed calcification rate of the valve and annulus compared to other aortic valves. As a result, the implantation of a TAVI, under such conditions, has several major clinical disadvantages such as the occurrence of paravalvular leaks, which leaks may be significant, or the migration of the TAVI implant.

In order to obtain good results with TAVI, it is very important to place the valve on a surface that is as regular as possible in order to avoid a distortion susceptible of rendering the opening of the prosthesis incompatible, the aim being to minimize the paravalvular leaks which in different ways affect at least 80% of TAVIs'.

Based on the analysis of this state of the art, one of the problems addressed by the invention is to make available a device suitable for removing calcified tissue and vegetation from within and above the leaflets of the aortic valve by implantation of an aortic valve by TAVI. Therefore, the aim is to permit partial or complete ablation of the calcium from the valves by a transcatheter approach and thereby optimizing the surface with a view to implantation of the valve.

To solve this problem and achieve these goals, a transcatheter device has been conceived and developed for the ablation of calcified leaflets of a native aortic valve, which device comprises a soft body serving as a catheter and having a soft and flexible endpiece engaging with a guide wire previously inserted and suitable for passing through the leaflets of the valve above the part where the calcified tissue needs to be removed, said endpiece having at least one cutting system mounted in combination with a vacuum suction means, said endpiece being equipped with an adjustable guide means suitable for engaging with the calcified tissue over the course of the ablation operation performed by the cutting system in combination with a spiral path effect applied to the endpiece.

It is clear from the features of the invention that the transcatheter ablation device is designed to be introduced directly from the aortic root with direct puncturing of the ascending aorta, for example with trans-aortic access via a small thoracotomy, or with an endoscopy trocar, or with transcatheter access via the femoral artery, or with access via other peripheral vessels.

To solve the problem of ensuring perfect contact of the cutting system by the ablation of the calcified tissue, resulting in optimal decalcification, the adjustable guide means is a soft ribbon suitable for being deployed in a circular manner in order to become in contact with the calcified tissue.

It should be noted that it is possible to adjust the expansion of the soft band in such a way as to progressively spread open the decalcified zone, always in a circular manner. It will also be noted that, after the ablation of the tissue has been performed, the length of the deployed ribbon provides a correct evaluation of the diameter of the aortic root, thus permitting the selection of the suitable size of TAVI implant.

Advantageously, the ribbon is deployed in an eccentric manner with respect to the endpiece.

In one embodiment, the ribbon is mounted in combination, on the one hand, with a rotary shaft actuated by a maneuvering element accessible from outside the catheter and on the other hand, with a stationary part of the catheter from which said ribbon is deployed under the effect of an action exerted on said maneuvering element in order to increase the diameter of the band until it comes into contact with the wall of the aortic valve.

One of the ends of the ribbon is fixed to the rotary shaft so as to be wound around the latter and protrude through an opening of the catheter, in order to be fixed by its other end in the part of said catheter formed by a slit, so as to allow said ribbon to protrude in an eccentric manner.

To solve the problem of cutting and removing the calcified leaflets and the surrounding tissues, the cutting system has two motorized rotary cutting heads arranged coaxially one above the other, the head located at the end of the endpiece, and serving first to remove the calcified tissue, having arrangements suitable for performing a rough cut by grinding, while the other head has arrangements suitable for performing a fine cut by grinding. The cutting heads protrude laterally from the endpiece in a manner parallel to the generatrices thereof.

Advantageously, the suction means is synchronized with the driving of the cutting heads, the tissue debris being evacuated via at least one suction conduit mounted inside the catheter.

According to other features, the flexible endpiece is made from a polymer material such as silicone, with radiopaque markers for monitoring its position in the operating zone.

The device comprises a dynamometric system suitable for measuring the aortic diameter where the valve is to be implanted under a given pressure, in a position in which the cutting system is maintained in contact with the calcified tissue by means of the ribbon.

As has been indicated, the decalcifying device can be introduced directly into the aortic root with direct puncturing of the ascending aorta or by a transfemoral transcatheter approach or other approaches, but it can also be positioned using introducers of all known and appropriate types.

Figure 2:
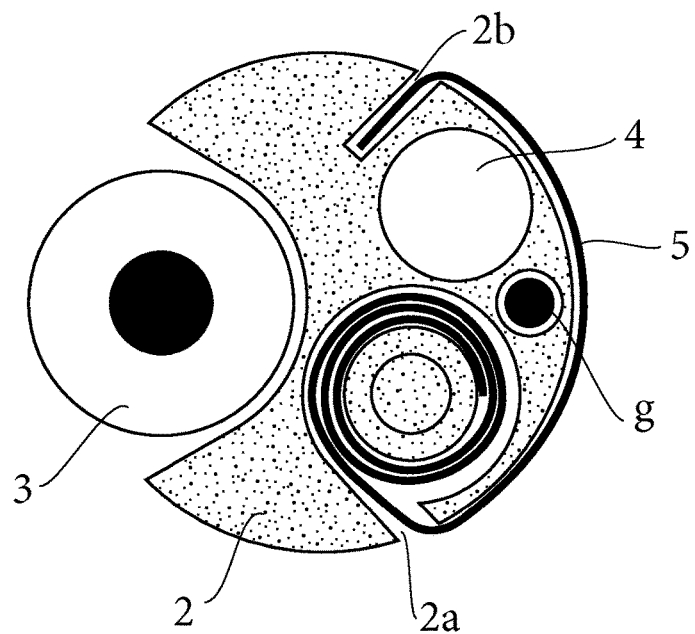
Figure 3:
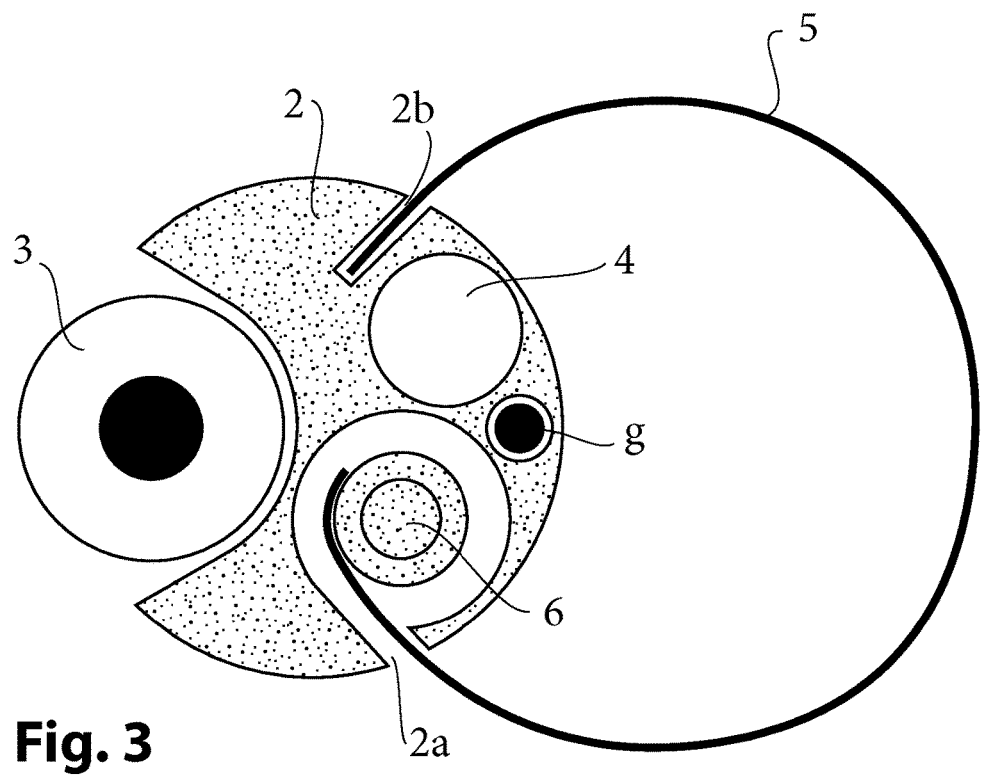

The invention is explained in more detail below with reference to the figures of the attached drawings, in which:

FIG. 1 is a perspective and partially sectioned view showing the active part of the transcatheter implantation device, FIG. 2 shows a very much enlarged and schematic cross-sectional view of the endpiece for the ablation and suction of debris before deployment of the positioning ribbon, FIG. 3 is a view corresponding to FIG. 2, after deployment of the positioning ribbon, FIGS. 4 to 17 show the main steps for transcatheter ablation of calcified tissue at the leaflets of a native aortic valve by means of the device according to the invention as illustrated in FIGS. 1, 2 and 3.

The ablation device is directly composed of a catheter with dimensions allowing it to be used in this type of procedure or inserted in an introducer catheter of any known and suitable type.

As it is illustrated in FIG. 1, in particular, the device comprises a soft body (1) serving as a catheter and having a soft and flexible endpiece (2) suitable for passing through the leaflets of the calcified native valve and above the part where the calcified material needs to be removed, said endpiece being able to engage with a guide wire (g). The endpiece (2) has at least one cutting system (3) mounted in combination with a vacuum suction means (4). The endpiece (2) is additionally equipped with an adjustable guide means (5) suitable for engaging with the calcified tissue over the course of the ablation operation performed by the cutting system (3) in combination with a spiral path effect applied to said endpiece (2).

As is indicated in the description below, the ablation of the tissue takes place along a spiral trajectory starting from the center and extending as far as the periphery of the valve by rotational translation against the edges of the tissue by way of the cutting system (3). The decalcification is obtained by applying a lateral pressure of the cutting system (3), in combination with the other guide means (5), on the calcified tissue, while avoiding cutting the aortic wall once the valve is completely cleaned.

The guide means (5) is composed of a soft ribbon suitable for being deployed in a circular manner in the position of contact with the calcified tissue. Advantageously, the ribbon (5) is deployed in an eccentric manner with respect to the endpiece (2) (FIGS. 2 and 3). In one embodiment, the ribbon (5) is mounted in combination, on the one hand, with a rotary shaft (6) controlled by a maneuvering element accessible from outside the catheter (1), and, on the other hand, with a stationary part of the endpiece (2) from which said ribbon (5) is deployed. More particularly, one of the ends of the ribbon (5) is fixed to the rotary shaft (6) so as to be wound around the latter and protrude through an opening (2a) of the endpiece (2), in order to be fixed by its other end on the stationary part of said endpiece. In the example illustrated, this stationary part is formed by a slit (2b), so as to allow said band to protrude in an eccentric manner (FIG. 3).

As will be described below, this ribbon (5) allows the cutting system (3) to be kept in contact with the remaining tissue removed under the effect of the eccentric movement of said band and of its increase in diameter, during the gradual decalcification along a spiral path. Given that the tissue ablation proceeds from the center of the native valve to the periphery thereof, it is important to have some contact between the cutting system and the calcified tissue.

The cutting system (3) has two motorized rotary cutting heads (3a) and (3b) arranged coaxially one above the other. The cutting heads (3a) and (3b) protrude laterally from the endpiece (2) in a manner parallel to the generatrices thereof. The head (3a), located at the end of the endpiece (2), and below the head (3b) in a vertical position of the catheter, is able to serve first to remove the calcified tissue since it has a toothed arrangement suitable for performing a rough cut by grinding. Conversely, the other head (3b), arranged above the head (3a), has arrangements suitable for performing a fine cut by grinding. These characteristics allow the operator to adapt the decalcification to the type and density of the calcified native valve and to achieve the results depending on the valve to be implanted.

Without departing from the scope of the invention, other cutting systems may be envisioned, for example ultrasonic systems.

The suction means is advantageously synchronized with the driving of the cutting system (3). This suction means, which may be of any known and suitable type, is under the control of a suction conduit (4) mounted inside the endpiece (2) and the catheter (1).

Figure 4:
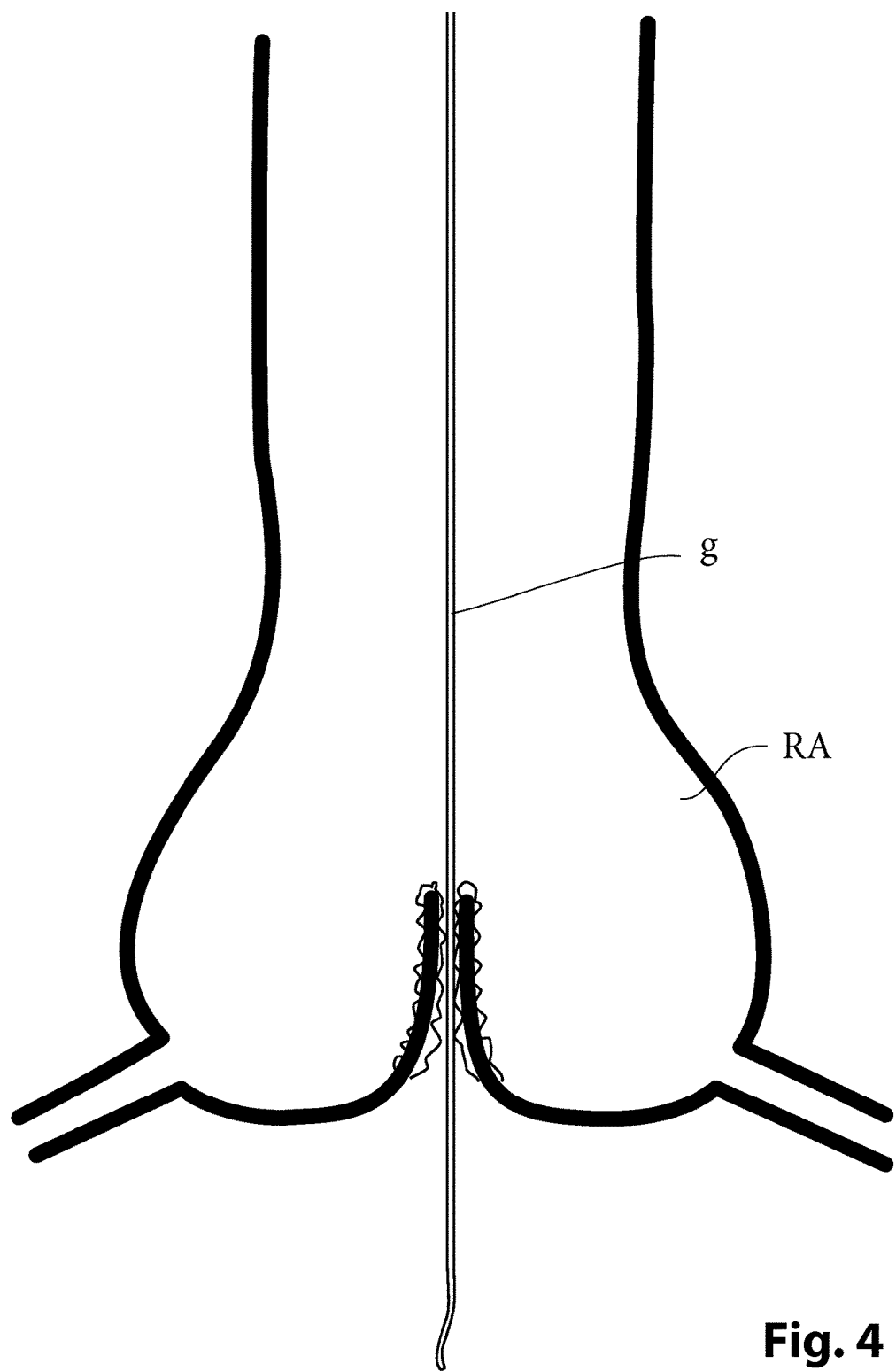

Reference is made to FIGS. 4 to 17 which show the different sequences for placement of the transcatheter device and for ablation of the calcified tissue at the leaflets of the native aortic valve. FIG. 4 shows the aortic root after placement of the guide wire (g) which, in a known manner, is engaged in order to pass through the stenosed aortic valve.

Figure 5:
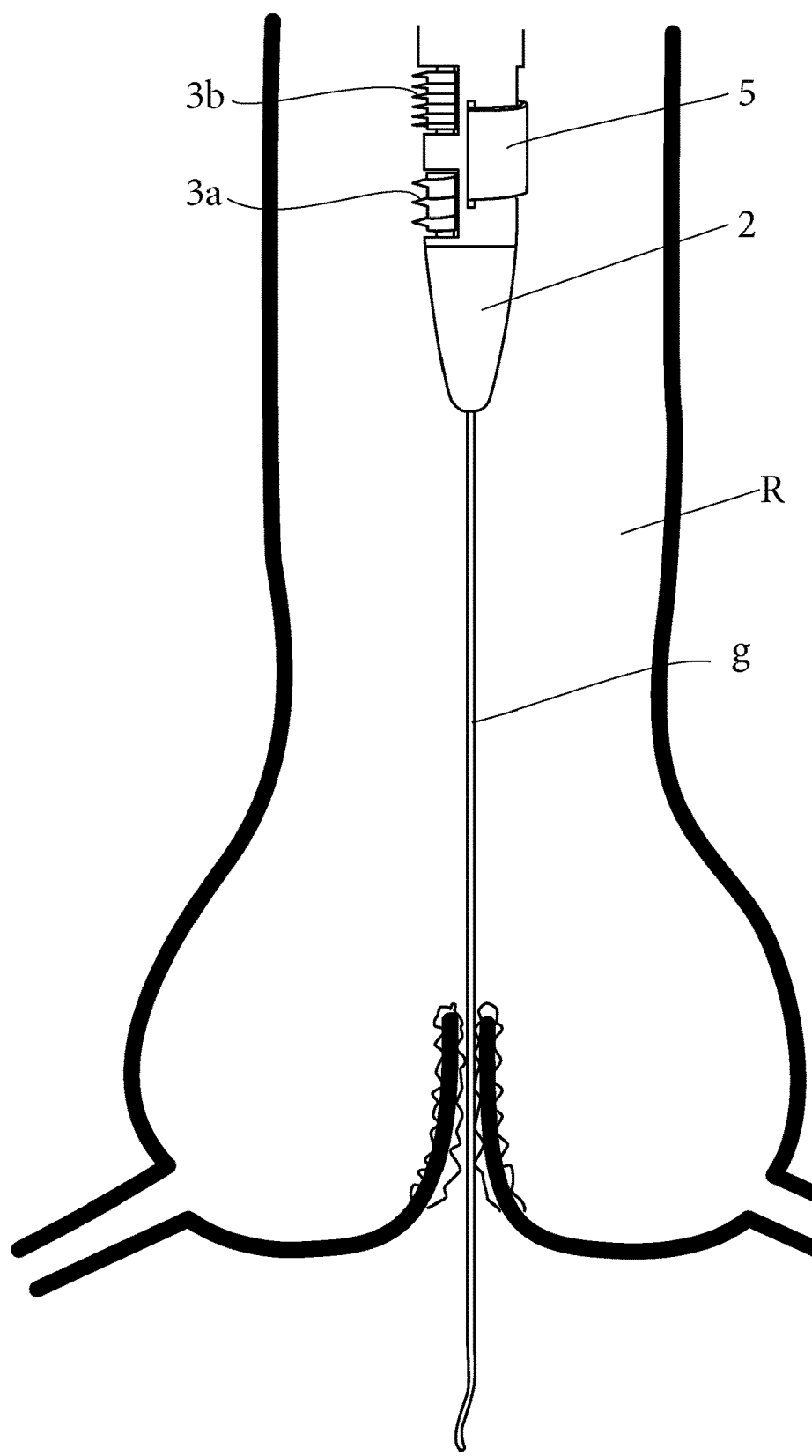
Figure 6:
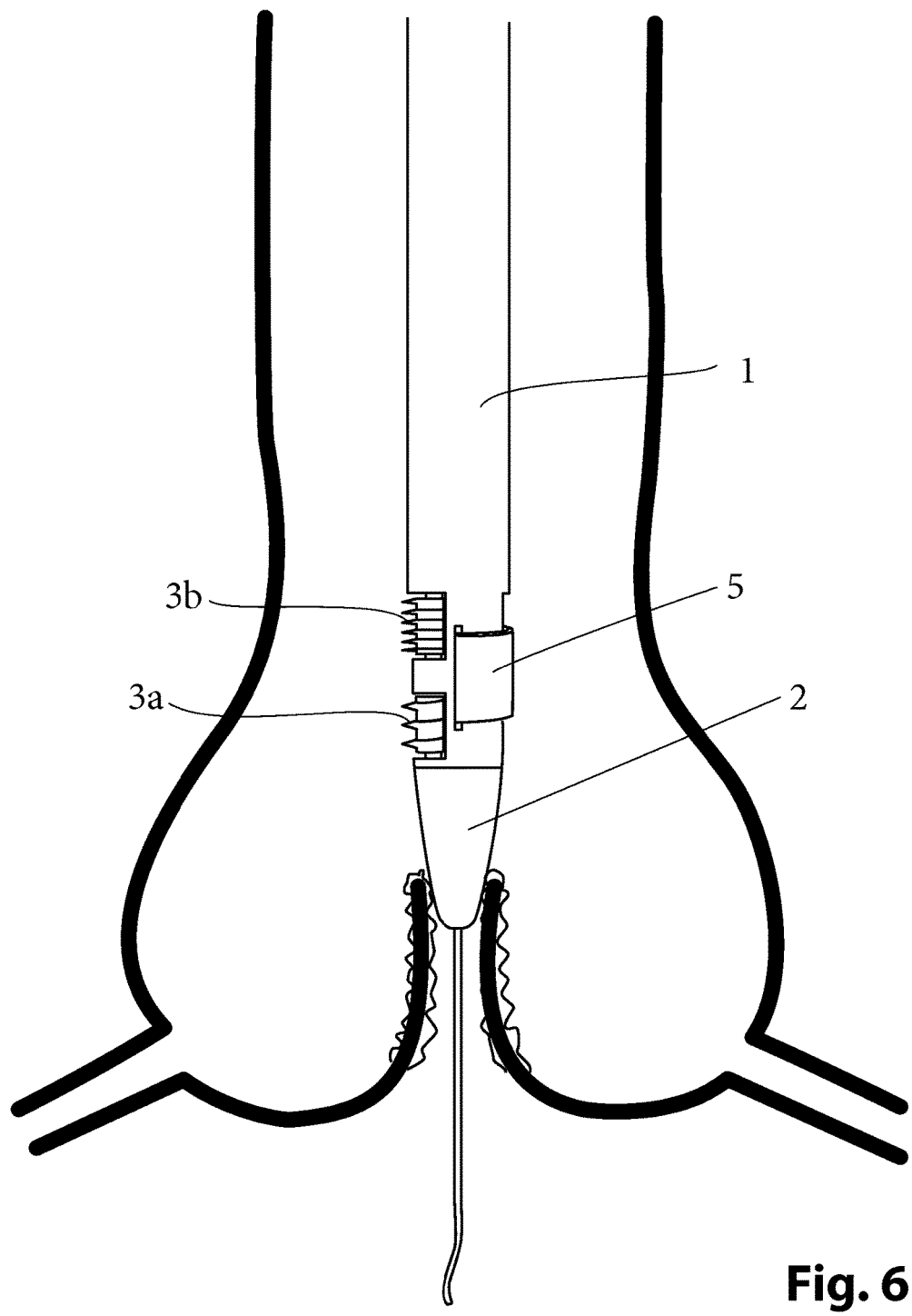
Figure 7:
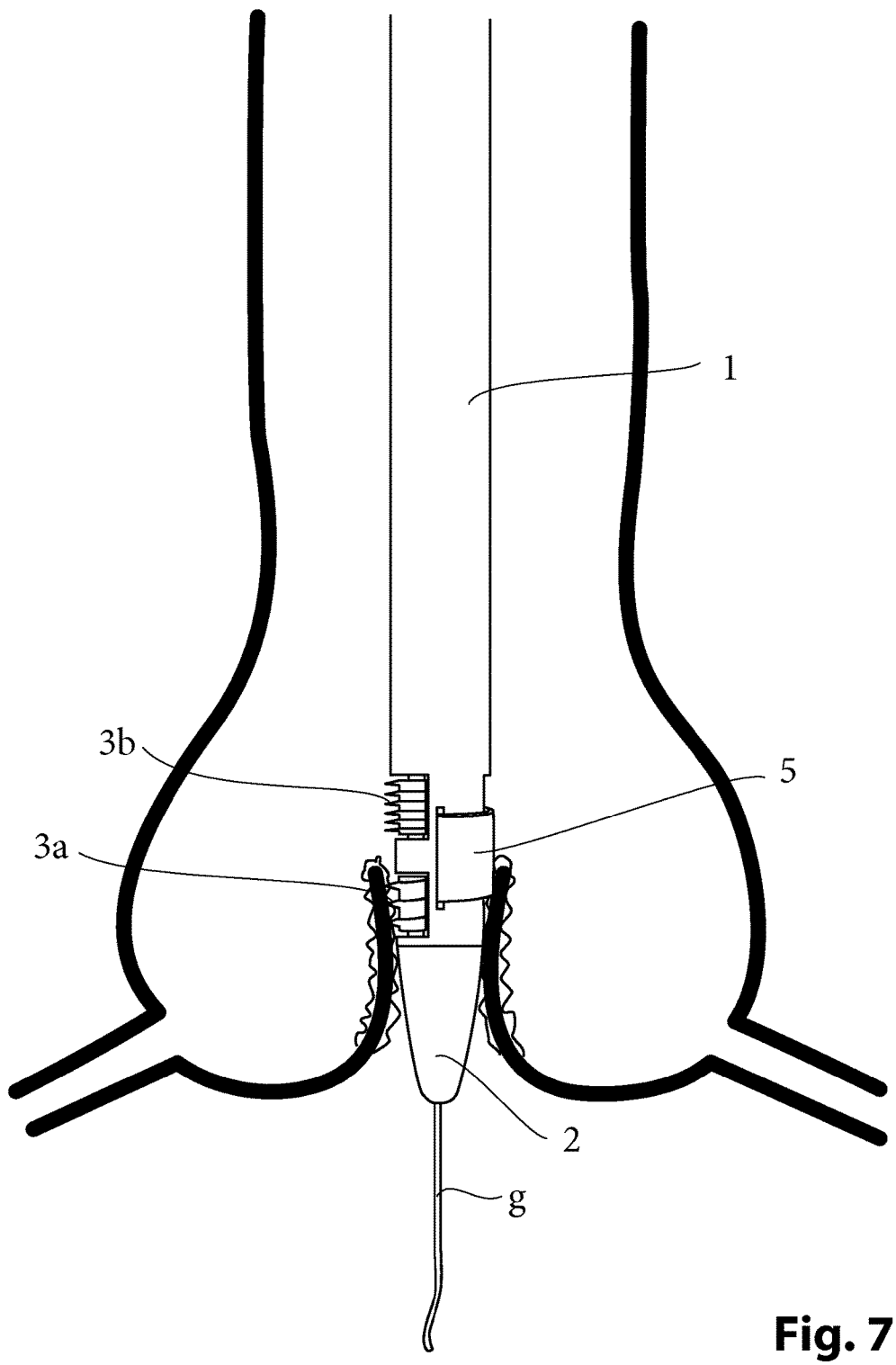
Figure 8:
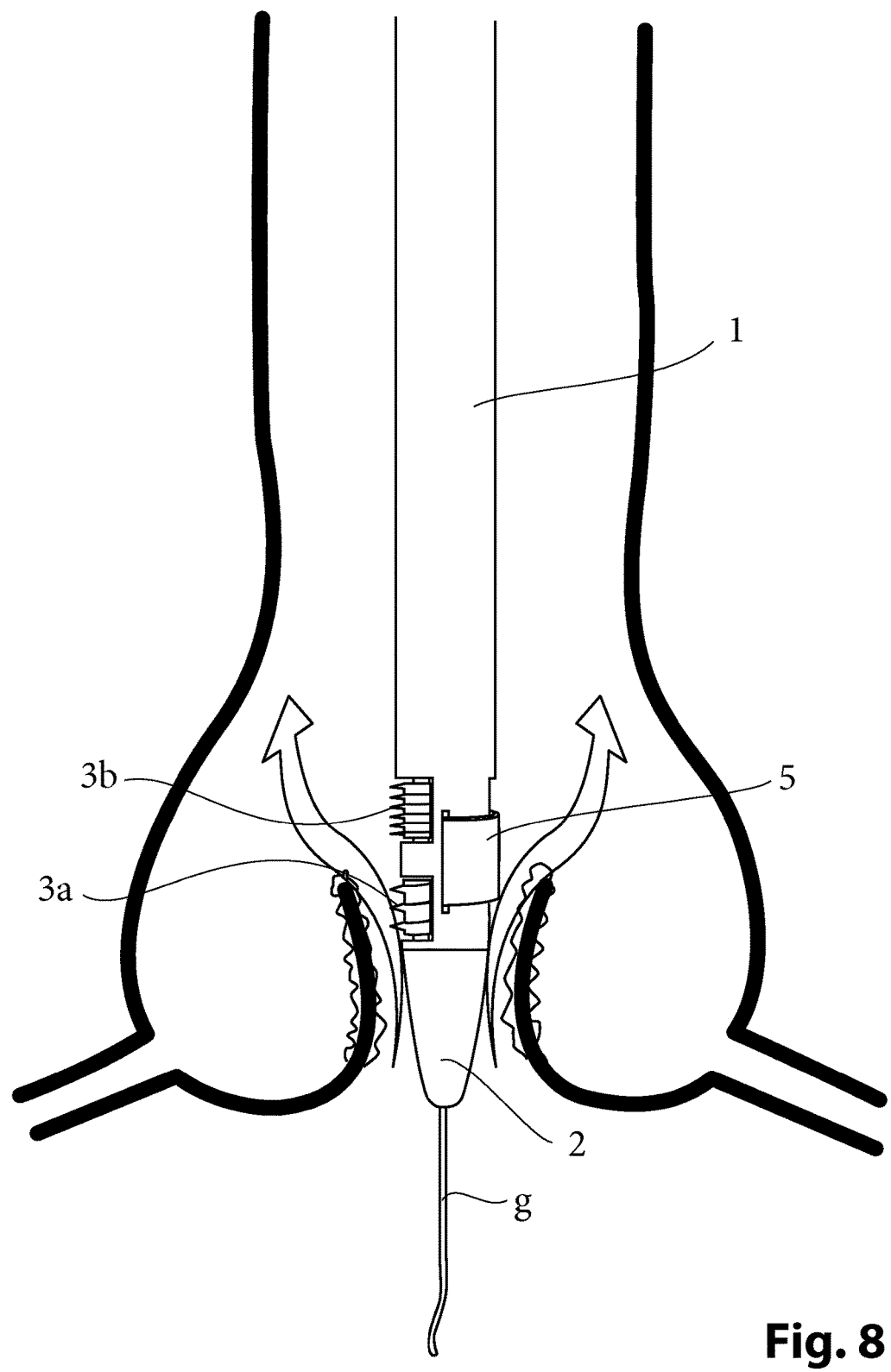
Figure 9:
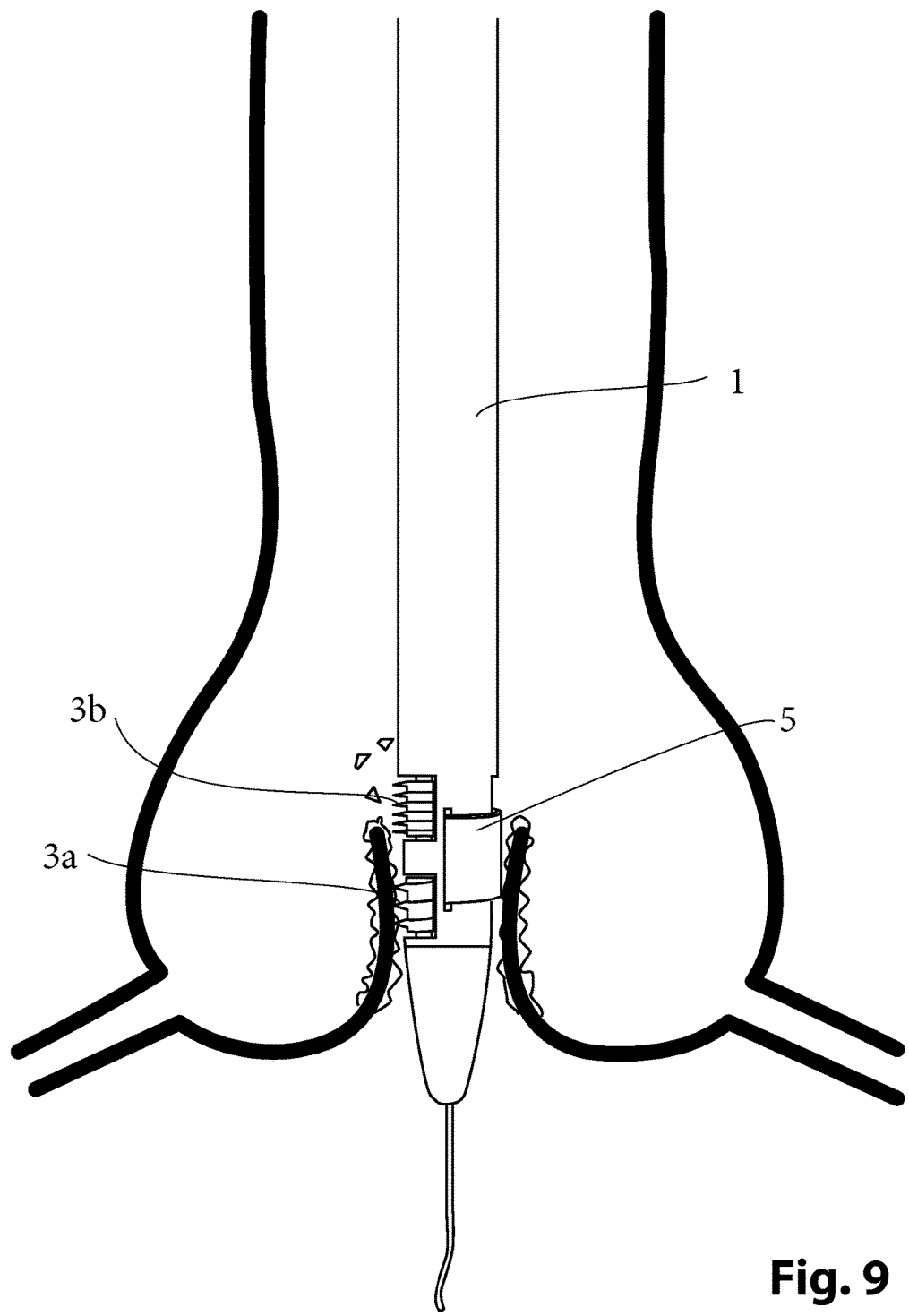
Figure 10:
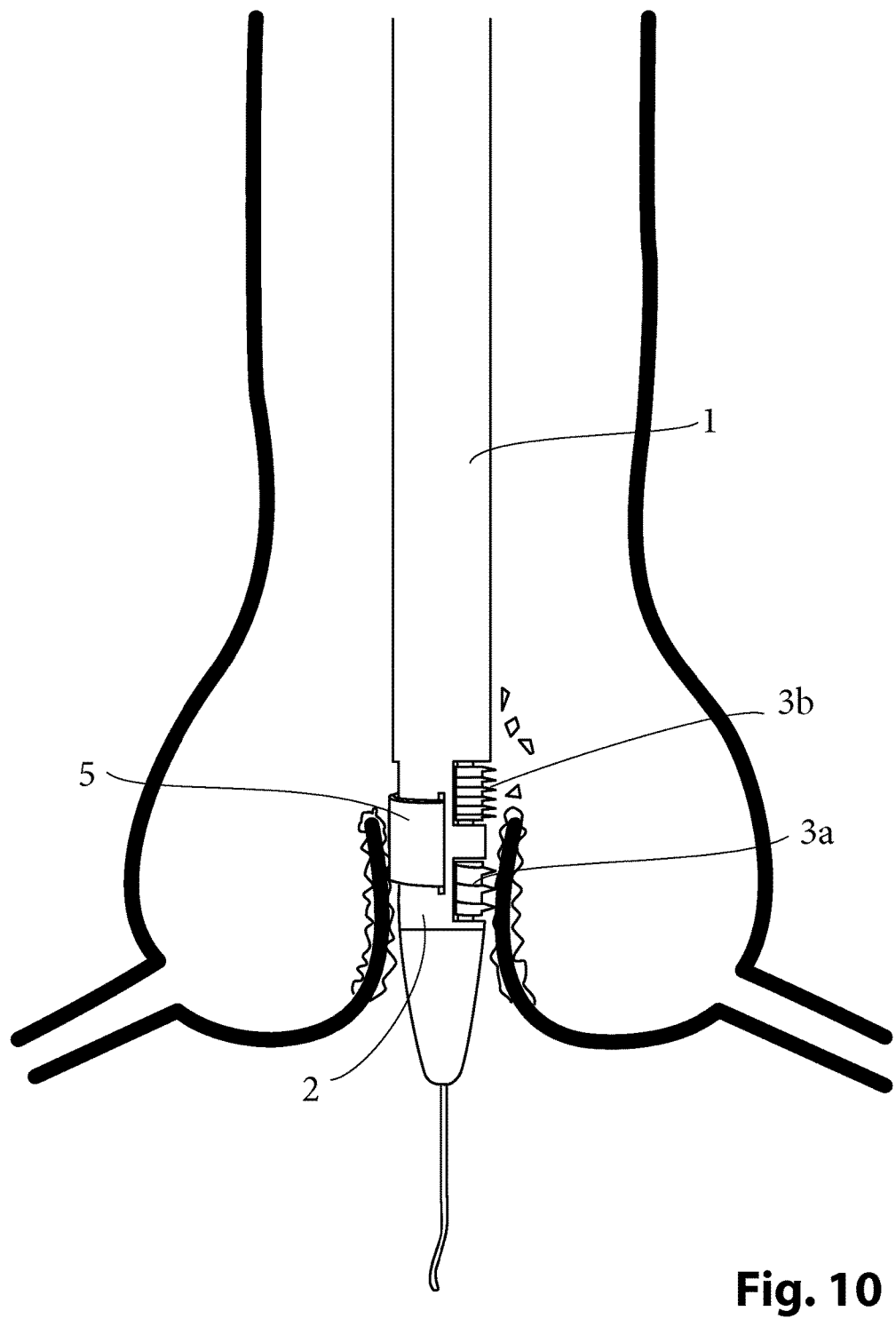

The transcatheter device in the form of a flexible tube (1), for example, with its endpiece (2), is inserted, by association with the guide wire (g), in order to be directed above the part where the calcification is to be removed (FIGS. 5 and 6). Radiopaque marking identifies, under fluoroscopy and under TEE, the ablation part on the catheter (1). One marker is placed above the aortic valve and the other marker below.

Figure 11:
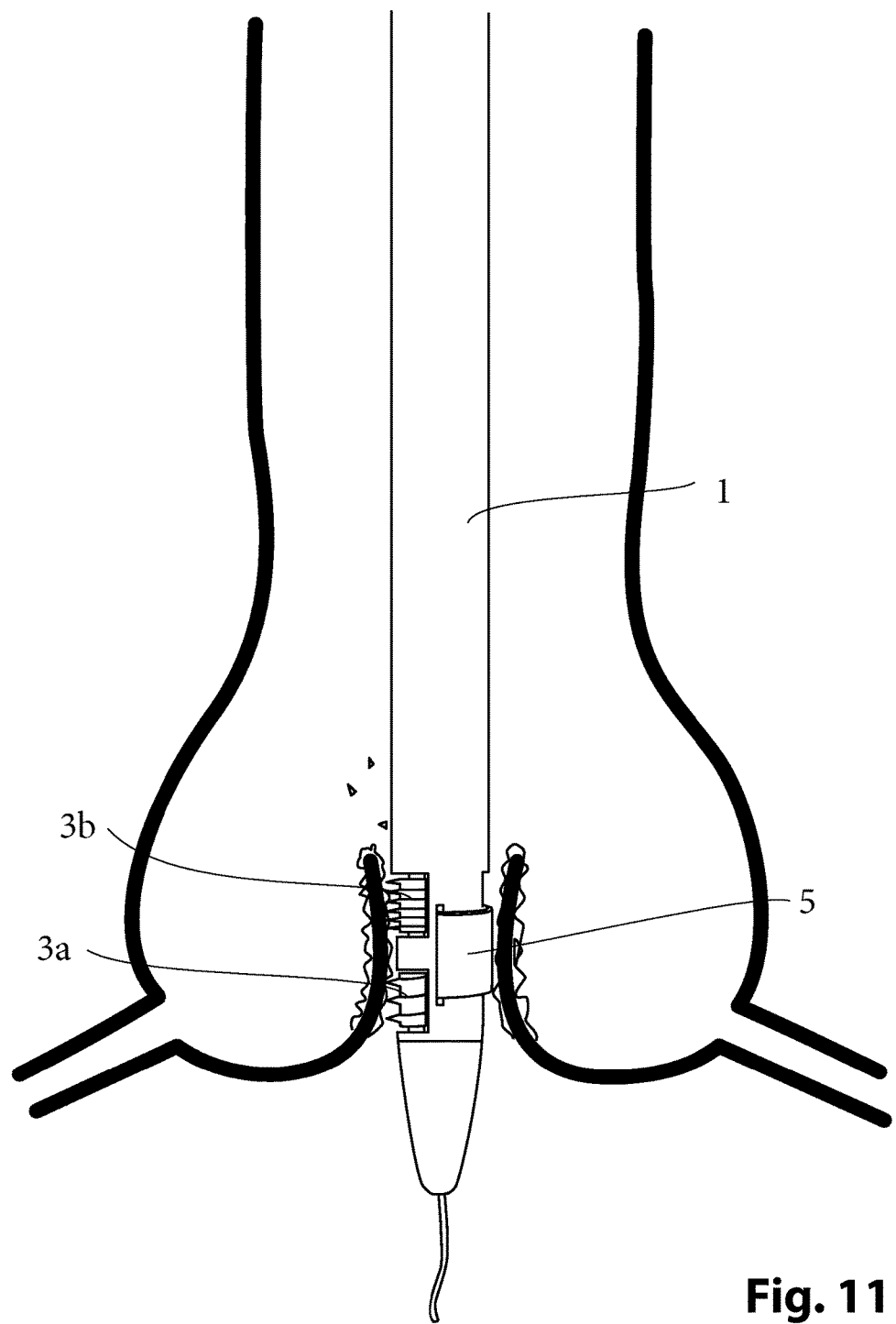
Figure 12:
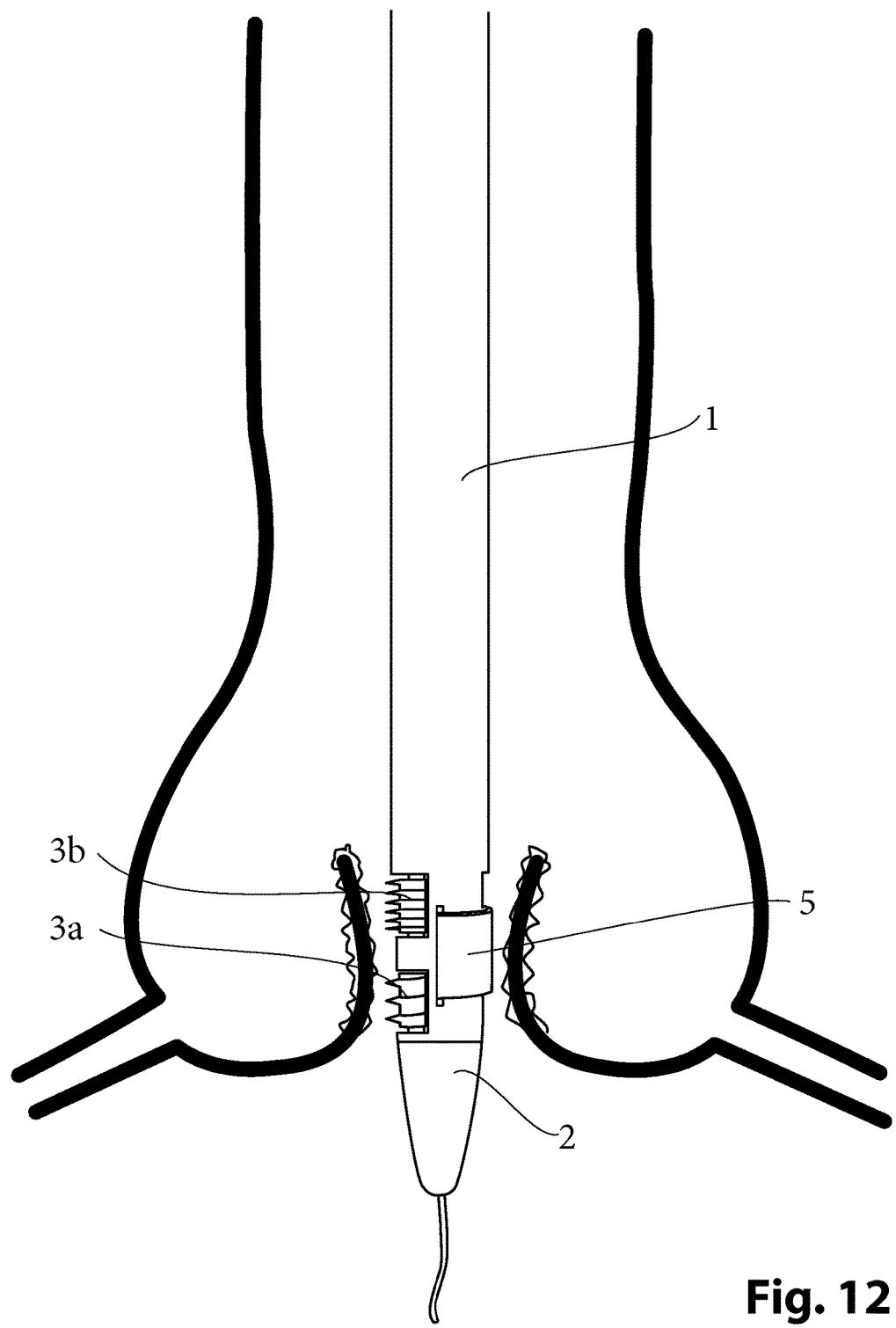

The ablation procedure as such can commence by first using the cutting head (3a) with the rough teeth (FIGS. 7 and 8), then the cutting head (3b) with the fine teeth (FIG. 11).

Figure 13:
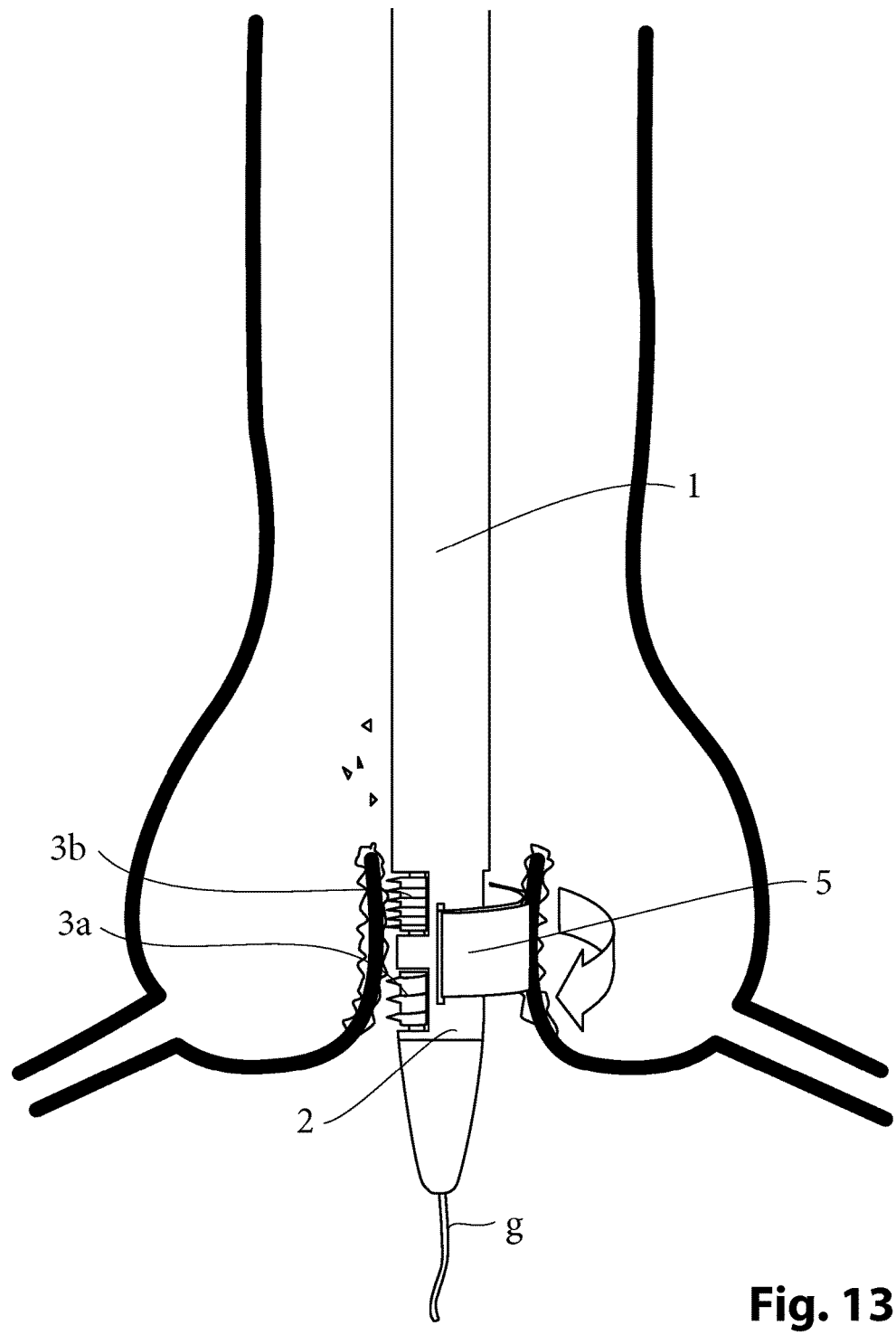
Figure 14:
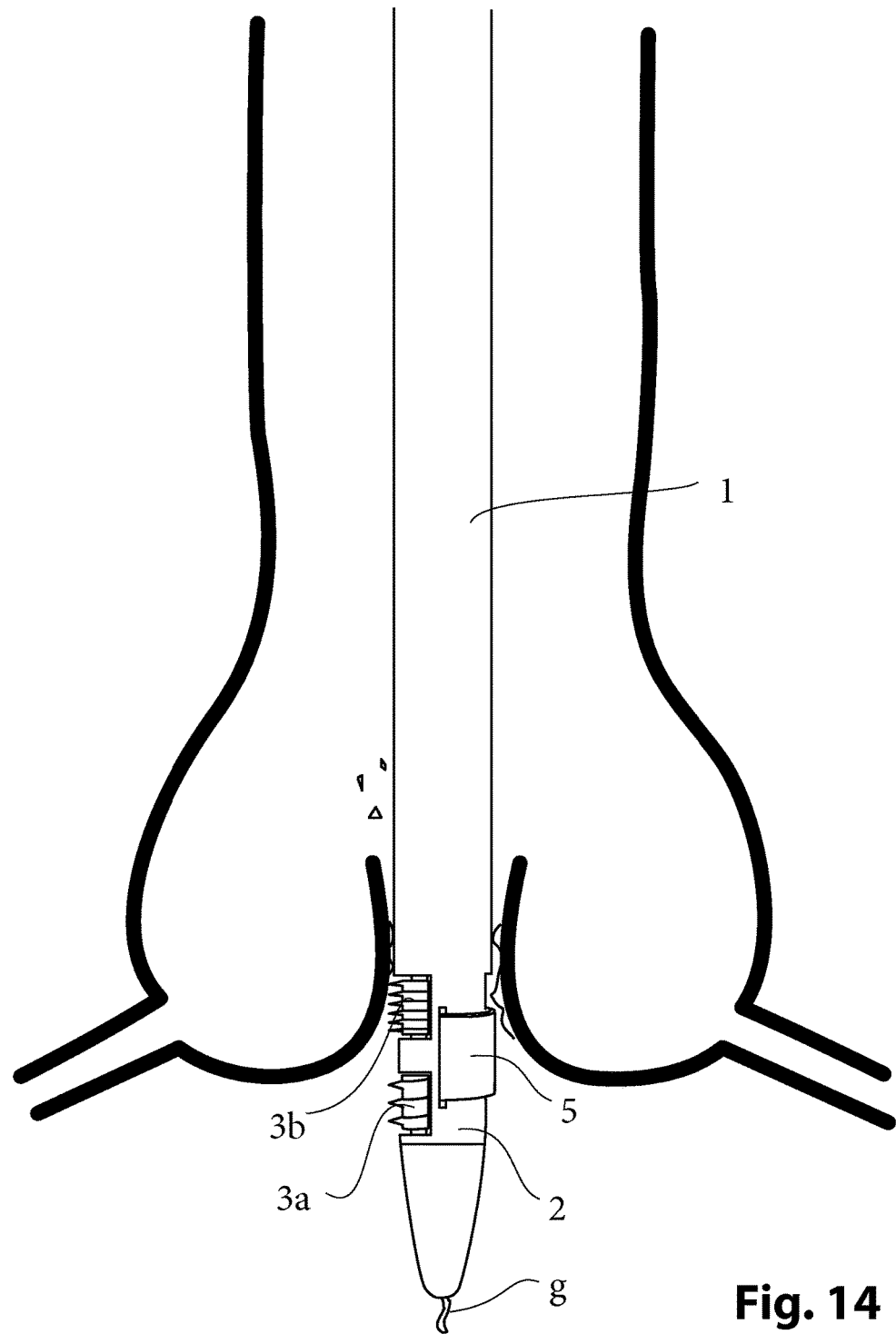
Figure 15:
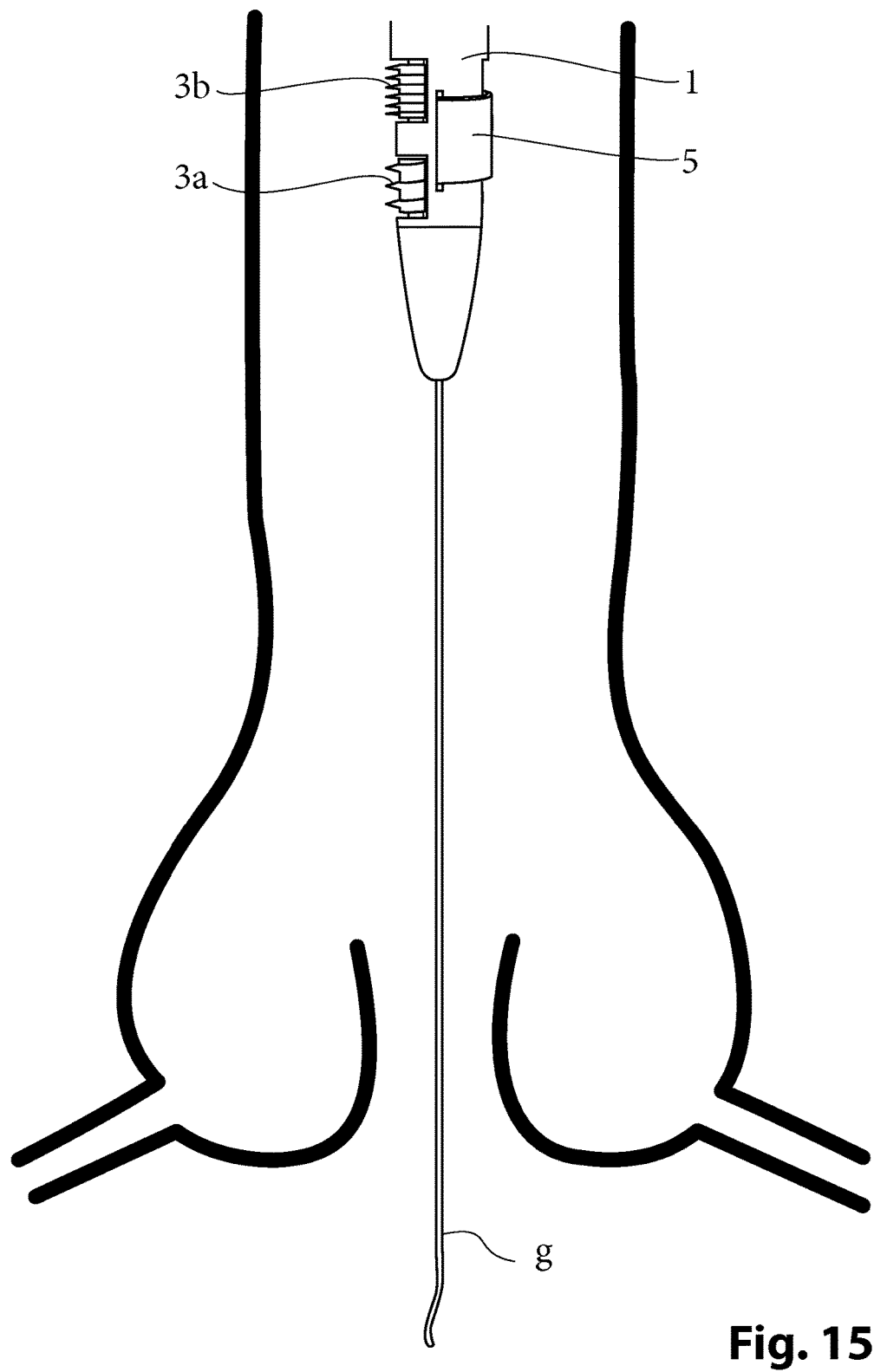
Figure 16:
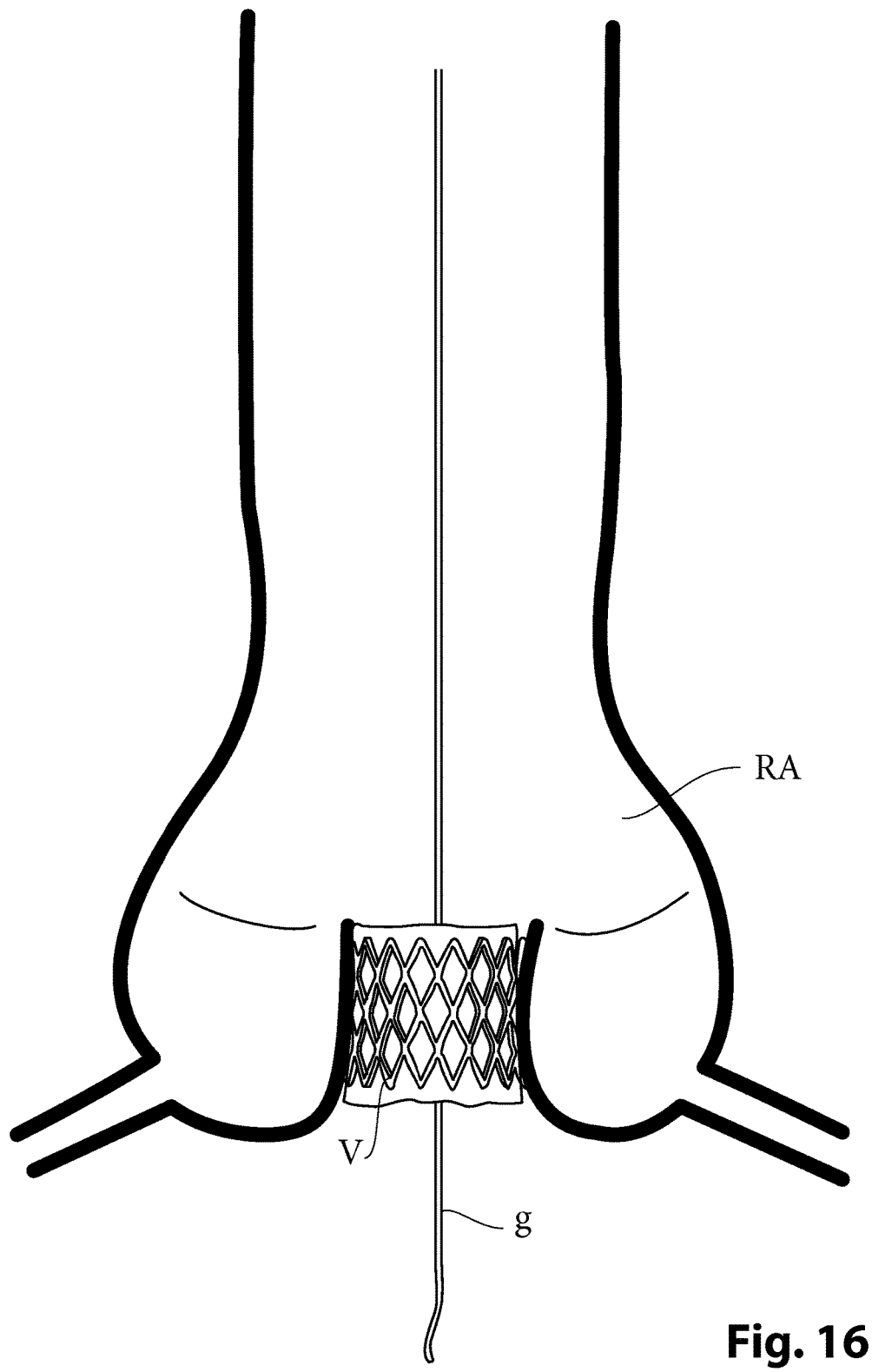
Figure 17:
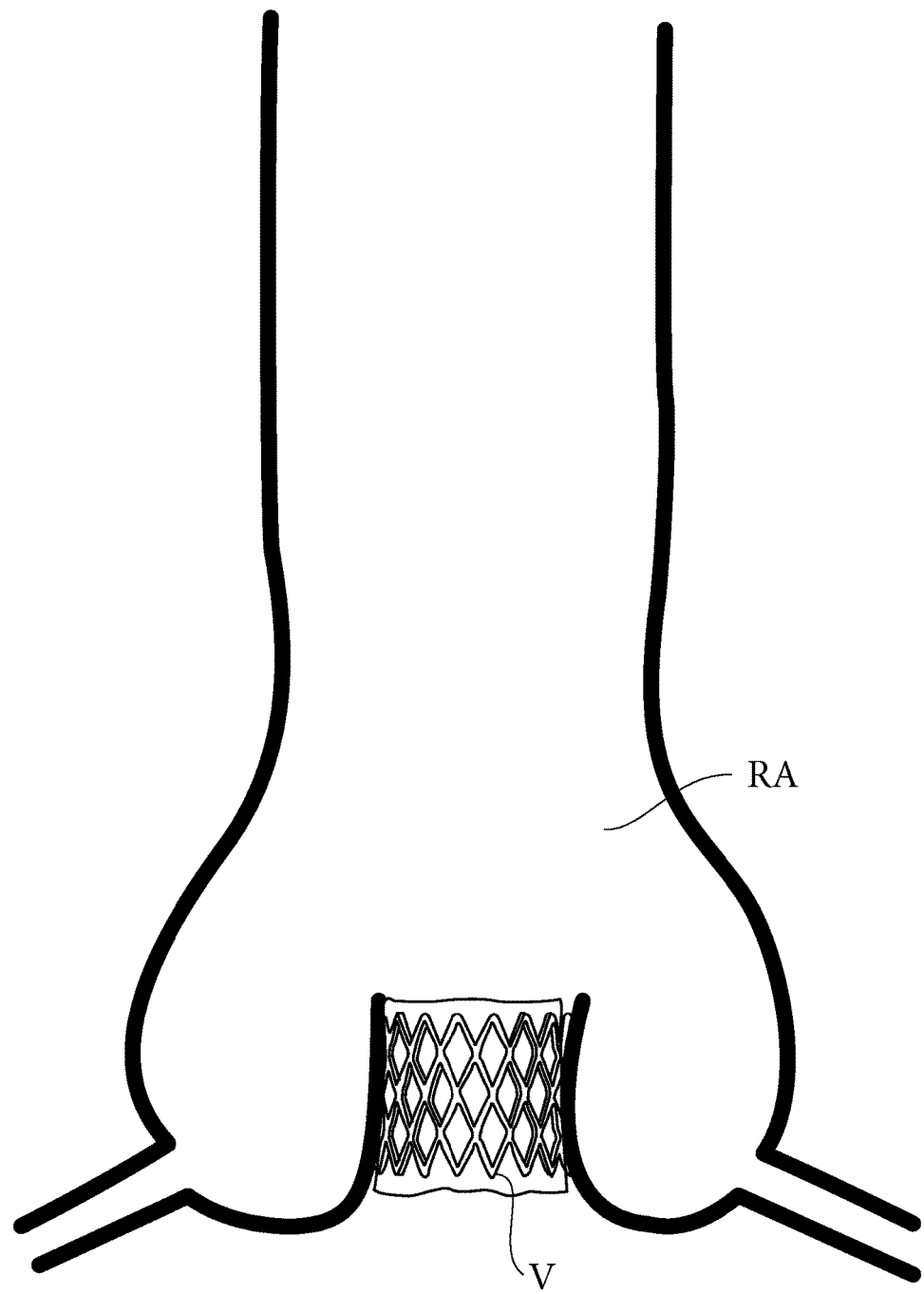

The procedure for ablation of the calcified tissue starts from the center of the native valve (FIG. 9) and proceeds in a spiral path with progressive rotation of the ablation head (FIGS. 10 and 11), in combination with the ribbon (5) which is deployed eccentrically in order to maintain continuous contact of the cutting head (3) with the calcified tissue (FIG. 13). The cutting head with the fine teeth (3b) can then be used to remove the calcified tissue (FIG. 14).

As indicated, during the decalcification procedure, the suction system (4) is operated in such a way as to be synchronized with the cutting system (3) in order to evacuate the calcium debris and the fibers of the leaflets of the native valve through a suction conduit situated inside the catheter (1).

This suction is particularly important given that the intervention is performed in the circulating blood and not in an extracorporeal circuit.

The decalcification procedure as such can be continued until the native leaflets are sufficiently thin, or until complete ablation of the leaflets is achieved in order to leave a clean aortic root in view of an implantation of a specific aortic valve prosthesis.

Advantageously, when the calcium ablation procedure has been completed, the operator is able to measure the diameter of the aortic root using the ribbon (5). This ribbon can in fact be equipped with a measuring system and a dynamometer, making it possible to measure the diameter of the aortic root under specific pressure, the reading being visible from outside the catheter. The fact that this aortic root is under a specific pressure is important given that this condition provides information, required by the operator, on the residual elasticity of the aortic ring, which has been partially or completely decalcified, in order to choose the correct size and the correct valve prosthesis.

Once the decalcification operation has been completed, the catheter is removed (FIG. 16), and the TAVI valve is put in place (FIGS. 16 and 17) by means of an introducer.

The advantages are clear from the description.

The invention claimed is:

1. A transcatheter device for ablation of calcified tissue at leaflets of an aortic valve comprising:
   a catheter having a soft body and having a soft and flexible endpiece configured to engage with a guide wire and suitable for passing through the leaflets where the calcified tissue needs to be removed;
   a cutting system attached to the endpiece and including two motorized rotary cutting heads arranged coaxially one above the other; and
   a vacuum suction device arranged in combination with the cutting system, wherein
   one of the motorized rotary cutting heads is located at an end of the endpiece and is configured to remove the calcified tissue and to perform a rough cut by grinding, and
   the other one of the motorized rotary cutting heads is configured to perform a fine cut by grinding,
   the endpiece having an adjustable guide for engaging with the calcified tissue during the ablation performed by the cutting system and for applying a spiral path effect to the endpiece.

2. The device as claimed in claim 1, wherein the adjustable guide includes a soft ribbon for deploying in a circular manner at a position of contact with the calcified tissue.

3. The device as claimed in claim 2, wherein the soft ribbon is deployable in an eccentric manner with respect to the endpiece.

4. The device as claimed in claim 2, wherein the soft ribbon is mounted in combination with a rotary shaft actuated by a maneuvering element accessible from outside the catheter, and is mounted with a stationary part of the endpiece from which the soft ribbon is deployed wherein the maneuvering element is configured to increase a diameter of a band from a deployed soft ribbon.

5. The device as claimed in claim 4, wherein one end of the ribbon is fixed to the rotary shaft so as to be wound around the rotary shaft and protrude through an opening of the endpiece, and the other end of the ribbon is fixed to the stationary part of the endpiece formed by a slit, to allow the band to protrude in an eccentric manner.

6. The device as claimed in claim 2, further comprising:
   a dynamometric system configured to measure an aortic diameter where the valve is to be implanted under a given pressure, in a position in which the cutting system is maintained in contact with the calcified tissue by the ribbon.

7. The device as claimed in claim 1, wherein the two motorized rotary cutting heads protrude laterally from the endpiece.

8. The device as claimed in claim 1, wherein an operation of the vacuum suction device is synchronized with a driving of the motorized rotary cutting heads, and wherein a suction conduit is mounted inside the catheter.

9. The device as claimed in claim 1, wherein the endpiece is made from a polymer material, with a radiopaque marker for monitoring a position of the endpiece in an operating zone.

10. The device as claimed in claim 9, wherein polymer material includes silicone.

* * * * *